US012766345B2

(12) United States Patent
Kang et al.

(10) Patent No.: US 12,766,345 B2
(45) Date of Patent: Oct. 20, 2026

(54) ULTRASONIC SIGNAL GENERATION METHOD FOR CAVITATION BUBBLE CONTROL AND ULTRASONIC TREATMENT DEVICE USING SAME

(71) Applicant: ALPINION MEDICAL SYSTEMS CO., LTD., Seoul (KR)

(72) Inventors: Kook Jin Kang, Seoul (KR); Won Seok Lee, Seoul (KR); Hyeon Peel Choi, Seoul (KR); Seong Ho Kim, Seoul (KR)

(73) Assignee: ALPINION MEDICAL SYSTEMS CO., LTD., Seoul (KR)

( * ) Notice: Subject to any disclaimer, the term of this patent is extended or adjusted under 35 U.S.C. 154(b) by 0 days.

(21) Appl. No.: 19/209,721

(22) Filed: May 15, 2025

(65) Prior Publication Data

US 2025/0276199 A1 Sep. 4, 2025

Related U.S. Application Data

(63) Continuation of application No. PCT/KR2023/006761, filed on May 18, 2023.

(30) Foreign Application Priority Data

Nov. 25, 2022 (KR) ........................ 10-2022-0160569

(51) Int. Cl.
*A61N 7/00* (2006.01)

(52) U.S. Cl.
CPC ........ *A61N 7/00* (2013.01); *A61N 2007/0039* (2013.01); *A61N 2007/0052* (2013.01); *A61N 2007/0073* (2013.01)

(58) Field of Classification Search
CPC .............. A61N 7/00; A61N 2007/0039; A61N 2007/0052; A61N 2007/0073; A61N 2007/0065; A61N 2007/0078; A61N 2007/0095; A61N 7/02; A61B 8/00; A61B 8/08; A61B 8/0833; A61B 8/085; A61B 8/4477; A61B 8/4483
See application file for complete search history.

(56) References Cited

U.S. PATENT DOCUMENTS

| | | | |
|---|---|---|---|
| 10,219,815 B2 | 3/2019 | Maxwell et al. | |
| 2011/0054363 A1* | 3/2011 | Cain | A61B 8/00 601/4 |
| 2020/0282239 A1 | 9/2020 | Bader et al. | |

FOREIGN PATENT DOCUMENTS

| | | |
|---|---|---|
| JP | 2011-235173 A | 11/2011 |
| JP | 2013-503005 A | 1/2013 |
| JP | 2014-094172 A | 5/2014 |

(Continued)

*Primary Examiner* — Joel Lamprecht
(74) *Attorney, Agent, or Firm* — NKL LAW; Jae Youn Kim

(57) ABSTRACT

Provided is an ultrasonic signal generation method for cavitation bubble control, and the ultrasonic signal generation method for cavitation bubble control may include determining transmission ratios of a first frequency ultrasonic signal and a second frequency ultrasonic signal, generating the first frequency ultrasonic signal toward a target area so that a cavitation bubble expands in the target area based on the transmission ratios, and generating the second frequency ultrasonic signal toward the target area so that expansion of the cavitation bubble stops based on the transmission ratios.

16 Claims, 8 Drawing Sheets

(56) References Cited

FOREIGN PATENT DOCUMENTS

| | | | |
|---|---|---|---|
| KR | 10-2015-0064012 | A | 6/2015 |
| KR | 10-2017-0027652 | A | 3/2017 |
| WO | 2005-094701 | A1 | 10/2005 |

* cited by examiner (a)

(b)

ULTRASONIC SIGNAL GENERATION METHOD FOR CAVITATION BUBBLE CONTROL AND ULTRASONIC TREATMENT DEVICE USING SAME

TECHNICAL FIELD

The present disclosure relates to an ultrasonic signal generation method for cavitation bubble control and an ultrasonic treatment device using the same.

BACKGROUND ART

High-Intensity Focused Ultrasound (HIFU) is generally used to treat (process) living tissues such as cancer, tumors, and lesions. In other words, the treatment method using high-intensity ultrasound is a method that focuses high-intensity ultrasound on one spot and transmits the high-intensity ultrasound to use the heat generated to necrose the relevant living tissue. In this case, the high-intensity ultrasound should be controlled to avoid damaging healthy living tissue, and treatment (processing) using high-intensity ultrasound may avoid the incision process due to surgery.

Meanwhile, a histotripsy technology is a high-intensity focused ultrasound technology using a non-thermal method. This technology is a method of treating living tissue by generating cavitation bubbles in a target area by controlling the pressure and frequency of high-intensity focused ultrasound, and mechanically homogenizing lesions and tissues in the target area as the generated cavitation bubbles are generated, expanded, and collapsed. In the case of the histotripsy, it is possible to improve the problem of damage to surrounding tissues outside the target area caused by heat generated during treatment using conventional HIFU.

According to previous studies, the state (generation, expansion, reduction, elimination, or the like) of cavitation may be controlled according to the negative pressure or frequency that changes over time. However, in this case, since the treatment (removal) of lesions and tissues using cavitation bubbles should be stopped and the cavitation bubbles should be controlled, there may be a problem that the treatment efficiency may be somewhat reduced.

The technology underlying the present disclosure is disclosed in U.S. Pat. No. 10,219,815.

DISCLOSURE

Technical Problem

The present disclosure is intended to solve the problems of the related art as described above, and an object thereof is to provide an ultrasonic signal generation method for cavitation bubble control capable of removing a lesion in a target area by generating a cavitation bubble by applying a first frequency ultrasonic signal, and simultaneously eliminating the cavitation bubble in the target area by applying a second frequency ultrasonic signal while applying the first frequency ultrasonic signal, and an ultrasonic treatment device using the same.

The present disclosure is intended to solve the problems of the related art as described above, and an object thereof is to provide an ultrasonic signal generation method for cavitation bubble control that may increase treatment efficiency by simultaneously performing treatment of a lesion and cavitation bubble control using a plurality of frequencies, thereby resolving the problem of decreased treatment efficiency during frequency modulation time, and an ultrasonic treatment device using the same.

However, the technical tasks that the present disclosure seeks to accomplish are not limited to the technical tasks described above, and other technical tasks may exist.

Technical Solution

As a technical means for achieving the above technical task, an ultrasonic signal generation method for cavitation bubble control according to one embodiment of the present disclosure may include: determining transmission ratios of a first frequency ultrasonic signal and a second frequency ultrasonic signal; generating the first frequency ultrasonic signal toward a target area so that a cavitation bubble expands in the target area based on the transmission ratios; and generating the second frequency ultrasonic signal toward the target area so that the expansion of the cavitation bubble stops based on the transmission ratios.

According to one embodiment of the present disclosure, the generating of the first frequency ultrasonic signal and the generating of the second frequency ultrasonic signal may be performed simultaneously or alternately.

According to one embodiment of the present disclosure, in the generating of the first frequency ultrasonic signal, the first frequency ultrasonic signal may be transmitted according to a continuous cycle, and in the generating of the second frequency ultrasonic signal, when the second frequency ultrasonic signal is generated simultaneously with the generation of the first frequency ultrasonic signal, a first cycle at which the second frequency ultrasonic signal is transmitted and a second cycle at which the second frequency ultrasonic signal is not transmitted may be repeated to generate the second frequency ultrasonic signal.

According to one embodiment of the present disclosure, in the determining of the transmission ratios, a first transmission ratio for the first frequency ultrasonic signal and a second transmission ratio for the second frequency ultrasonic signal may be determined.

According to one embodiment of the present disclosure, in the determining of the transmission ratios, a combination ratio of the first frequency ultrasonic signal and the second frequency ultrasonic signal may be determined so that the sum of a first transmission ratio for the first frequency ultrasonic signal and a second transmission ratio for the second frequency ultrasonic signal is 1 (100%).

According to one embodiment of the present disclosure, the first frequency ultrasonic signal may be a signal that generates the cavitation bubble in the target area or expands the cavitation bubble generated in the target area, and the second frequency ultrasonic signal may be a signal that stops the expansion of the cavitation bubble generated in the target area or reduces or eliminates the cavitation bubble generated in the target area.

According to one embodiment of the present disclosure, the ultrasonic signal generation method may further include transmitting a diagnostic ultrasonic wave to the target area and receiving an ultrasonic echo signal reflected from the target area to generate an ultrasonic image.

According to one embodiment of the present disclosure, in the generating of the ultrasonic image, at least one of a location of a lesion in the target area, whether the cavitation bubble in the target area is eliminated, and whether the lesion is removed may be monitored.

As a technical means for achieving the above technical task, an ultrasonic treatment device using an ultrasonic signal generation method for cavitation bubble control according to one embodiment of the present disclosure may include: a transmission ratio determination unit for determining transmission ratios of a first frequency ultrasonic signal and a second frequency ultrasonic signal; a first transducer for generating the first frequency ultrasonic signal toward a target area so that a cavitation bubble expands in the target area based on the transmission ratios; and a second transducer for generating the second frequency ultrasonic signal toward the target area so that the expansion of the cavitation bubble stops based on the transmission ratios.

According to one embodiment of the present disclosure, the first transducer and the second transducer may generate the first frequency ultrasonic signal and the second frequency ultrasonic signal simultaneously or alternately.

According to one embodiment of the present disclosure, the first transducer may transmit the first frequency ultrasonic signal according to a continuous cycle, and when the second frequency ultrasonic signal is generated simultaneously with the generation of the first frequency ultrasonic signal, the second transducer may repeat a first cycle at which the second frequency ultrasonic signal is transmitted and a second cycle at which the second frequency ultrasonic signal is not transmitted to generate the second frequency ultrasonic signal.

According to one embodiment of the present disclosure, the transmission ratio determination unit may determine a first transmission ratio for the first frequency ultrasonic signal and a second transmission ratio for the second frequency ultrasonic signal.

According to one embodiment of the present disclosure, the transmission ratio determination unit may determine a combination ratio of the first frequency ultrasonic signal and the second frequency ultrasonic signal so that the sum of a first transmission ratio for the first frequency ultrasonic signal and a second transmission ratio for the second frequency ultrasonic signal is 1 (100%).

According to one embodiment of the present disclosure, the first frequency ultrasonic signal may be a signal that generates the cavitation bubble in the target area or expands the cavitation bubble generated in the target area, and the second frequency ultrasonic signal may be a signal that stops the expansion of the cavitation bubble generated in the target area or reduces or eliminates the cavitation bubble generated in the target area.

According to one embodiment of the present disclosure, the ultrasonic treatment device may further include an image transducer that transmits a diagnostic ultrasonic wave to the target area and receives an ultrasound echo signal reflected from the target area to generate an ultrasonic image.

According to one embodiment of the present disclosure, the image transducer may monitor at least one of a location of a lesion in the target area, whether the cavitation bubble in the target area is eliminated, and whether the lesion is removed.

The above-described means of solving the problems are merely exemplary and should not be construed as limiting the present disclosure. In addition to the above-described exemplary embodiments, additional embodiments may exist in the drawings and detailed description of the disclosure.

Advantageous Effects

According to the above-described means for solving the problem of the present disclosure, it is possible to remove a lesion in the target area by generating the cavitation bubble by applying the first frequency ultrasonic signal, and simultaneously eliminate the cavitation bubble in the target area by applying the second frequency ultrasonic signal while applying the first frequency ultrasonic signal.

According to the above-described means for solving the problem of the present disclosure, it is possible to increase treatment efficiency by simultaneously performing treatment of a lesion and cavitation bubble control using a plurality of frequencies, thereby resolving the problem of decreased treatment efficiency during frequency modulation time.

However, the effects that can be obtained from the present disclosure are not limited to the effects described above, and other effects can exist.

DESCRIPTION OF MAIN REFERENCE NUMERALS OF DRAWINGS

Figure 1:
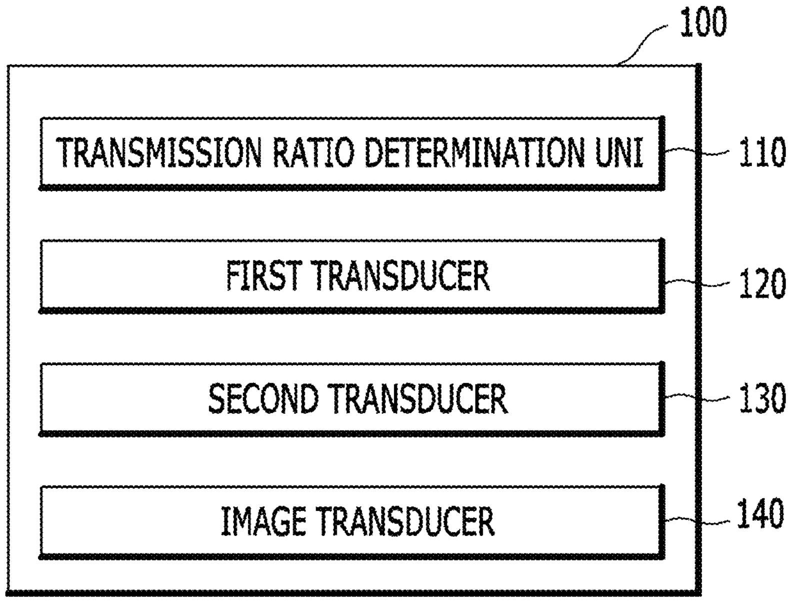
FIG. 1 is a schematic block diagram of an ultrasonic treatment device that applies an ultrasonic signal generation method for cavitation bubble control according to one embodiment of the present disclosure.

| | |
|---|---|
| 100: Ultrasonic treatment device using ultrasonic signal generation method for cavitation bubble control | |
| 110: Transmission ratio determination unit | 120: First transducer |
| 130: Second transducer | 140: Image transducer |
| F1: First frequency ultrasonic signal | F2: Second frequency ultrasonic signal |

BEST MODE

Below, with reference to the attached drawings, the embodiments of the present disclosure are described in detail so that those with ordinary knowledge in the technical field to which the present disclosure pertains may easily practice them. However, the present disclosure may be implemented in various different forms and is not limited to the embodiments described herein. In addition, in order to clearly describe the present disclosure in the drawings, parts that are not related to the description are omitted, and similar parts are given similar drawing reference numerals throughout the specification.

Throughout this specification, when a part is said to be "connected" to another part, this includes not only the case where it is "directly connected," but also the case where it is "electrically connected" or "indirectly connected" with another element in between.

Throughout the specification, when it is said that a member is located "on", "above", at an "upper end of", "below", at a "lower portion of", or at a "lower end of" another member, this includes not only cases where a member is in contact with another member, but also cases where another member exists between the two members.

Throughout this specification, whenever a part is said to "include" a component, this does not mean that it excludes other components, but rather that it may include other components, unless otherwise specifically stated.

The present disclosure relates to an ultrasonic signal generation method for cavitation bubble control and an ultrasonic treatment device using the same.

A high-intensity ultrasound described herein refers to ultrasound that is approximately 100,000 times stronger than the intensity of diagnostic ultrasonic wave. A high-intensity focused ultrasound (HIFU) treatment refers to a treatment method that burns and removes living tissue in a specific area by concentrating and transmitting high-intensity ultrasound to one place (a specific area) and using the high heat of 65° C. to 100° C. generated in the specific area. When high-intensity ultrasound that is approximately 100,000 times stronger than the intensity of diagnostic ultrasonic wave generally used for diagnosis is focused on one place (a specific area), heat is generated at the focus area. This is similar to the principle that heat is generated at the focus area when sunlight is focused with a convex lens, and since the ultrasound itself is harmless to the human body, heat is generated only at the focus where the ultrasound is concentrated, so there is no need to use a knife or needle, and it is a method of treating lesions in the body without general anesthesia.

In addition, in relation to this, the histotripsy technology described herein is a high-intensity focused ultrasound technology using a non-thermal method, which generates cavitation bubbles in a target area by controlling the pressure and frequency of the high-intensity focused ultrasound, and the generated cavitation bubbles are generated, expanded, and collapsed to mechanically homogenize lesions and tissues in the target area, thereby treating living tissues. In the case of the histotripsy, it is possible to improve the problem of damage to surrounding tissues outside the target area caused by heat generated during treatment using conventional HIFU.

In addition, the ultrasonic image described herein may mean a B-mode image or a C-mode image, or the like. The B-mode image may mean an image mode that represents the movement of an object, and the C-mode image may mean a color flow image mode. Meanwhile, the BC-mode image is an image mode that uses the Doppler effect to display the flow of blood or the movement of an object, and is a mode that provides both the B-mode image and the C-mode image, and is an image mode that provides anatomical information along with information on blood flow and the movement of the object. That is, the B-mode is an image mode that represents the movement of the object as a gray-scale image, and the C-mode is an image mode that represents the flow of blood or the movement of the object as a color flow image. The ultrasonic image according to one embodiment of the present disclosure is not limited to the B-mode image and the C-mode image.

Hereinafter, for convenience of explanation, the "ultrasonic signal generation method for cavitation bubble control and the ultrasonic treatment device 100 using the same" according to one embodiment of the present disclosure will be referred to as the "ultrasonic treatment device 100".

According to one embodiment of the present disclosure, the ultrasonic treatment device 100 may emit ultrasonic signals of different frequencies to a target area of a lesion, generate cavitation bubbles in the target area, and treat (remove) the lesion in the target area using the cavitation bubbles. In this case, the ultrasonic signals of different frequencies may be transmitted from different transducers or from one transducer depending on the frequency. A detailed description thereof will be given later.

According to one embodiment of the present disclosure, the ultrasonic treatment device 100 may include an ultrasonic probe (not illustrated), a device body (not illustrated), and a computer unit (not illustrated) that performs control of the ultrasonic probe (not illustrated). In this case, the computer unit (not illustrated) may mean a computing device, or the like, in which commands for controlling the operation of the ultrasonic probe (not illustrated) and the device body (not illustrated) are programmed.

FIG. 1 is a schematic block diagram of an ultrasonic treatment device that applies an ultrasonic signal generation method for cavitation bubble control according to one embodiment of the present disclosure.

Referring to FIG. 1, the ultrasonic treatment device 100 may include a transmission ratio determination unit 110, a first transducer 120, a second transducer 130, and an image transducer 140. However, the present disclosure is not limited thereto, and even when not disclosed herein, the ultrasonic treatment device 100 may include various components typically applied to an ultrasonic diagnostic device or an ultrasonic treatment device.

In this case, the transmission ratio determination unit 110 may be included in or correspond to the computer unit (not illustrated) described above, and the first transducer 120, the second transducer 130 and the image transducer 140 may be included in the ultrasonic probe (not illustrated) described above.

According to one embodiment of the present disclosure, the transmission ratio determination unit 110 may determine a transmission ratio of a first frequency ultrasonic signal F1 and a second frequency ultrasonic signal F2. In this case, the first frequency ultrasonic signal F1 may be a signal that generates a cavitation bubble in a target area of a lesion or expands a cavitation bubble already generated in the target area. In addition, the second frequency ultrasonic signal F2 may be a signal that stops the expansion of the cavitation bubble generated in the target area or reduces or eliminates the cavitation bubble generated in the target area.

For example, the first frequency ultrasonic signal F1 may be a signal having a frequency of about 3 MHz, and the second frequency ultrasonic signal F2 may be a signal having a frequency of about 6 MHz. However, the present disclosure is not limited thereto, and when the first frequency ultrasonic signal F1 is an ultrasonic signal having a frequency that may perform a role corresponding to the generation and expansion of the cavitation bubbles, and the second frequency ultrasonic signal F2 is an ultrasonic signal having a frequency corresponding to stop of expansion, reduction, and elimination of the cavitation bubbles, the characteristics of each frequency, such as frequency (Hz), period(s), and amplitude, may be changeable.

According to one embodiment of the present disclosure, the transmission ratio determination unit 110 may determine the transmission ratios of the first frequency ultrasonic signal F1 and the second frequency ultrasonic signal F2. For example, when the lesion in the target area needs to be removed, the transmission ratio determination unit 110 may generate and expand the cavitation bubble in the target area by increasing the ratio of the first frequency ultrasonic signal F1. However, when there is a possibility that the cavitation bubble in the target area is excessively generated or expanded and may cause damage to surrounding tissues other than the target area, the transmission ratio determination unit 110 may lower the ratio of the first frequency ultrasonic signal F1 and increase the ratio of the second frequency ultrasonic signal F2, thereby stopping the expansion of the cavitation bubble and further reducing or eliminating the excessively generated or expanded cavitation bubble.

According to one embodiment of the present disclosure, the transmission ratio for the first frequency ultrasonic signal F1 may be referred to as a first transmission ratio, and the transmission ratio for the second frequency ultrasonic signal F2 may be referred to as a second transmission ratio. In this case, when the intensity (size) ratio of the first frequency ultrasonic signal F1 that the ultrasonic treatment device 100 according to one embodiment of the present disclosure may transmit at maximum is 100%, and the intensity (size) ratio of the second frequency ultrasonic signal F2 is 100%, the transmission ratio determination unit 110 may determine the first transmission ratio at a ratio of 0% to 100%, and may determine the second transmission ratio at a ratio of 0% to 100%.

Specifically, the transmission ratio determination unit 110 may determine the first transmission ratio and the second transmission ratio. For example, when the transmission ratio determination unit 110 determines the first transmission ratio as 80% and the second transmission ratio as 40%, the first frequency ultrasonic signal F1 may be transmitted with an intensity (size) of 80% of the maximum ultrasonic signal that the ultrasonic treatment device 100 may transmit, and the second frequency ultrasonic signal F2 may be transmitted with an intensity (size) of 40% of the maximum ultrasonic signal that the ultrasonic treatment device 100 may transmit.

In addition, the transmission ratio determination unit 110 may determine a combination ratio of the first frequency ultrasonic signal F1 and the second frequency ultrasonic signal F2 such that the sum of the first transmission ratio for the first frequency ultrasonic signal F1 and the second transmission ratio for the second frequency ultrasonic signal F2 becomes 1 (100%). For example, when the transmission ratio determination unit 110 determines the first transmission ratio as 80% (0.8), the second transmission ratio may be determined as 20% (0.2), and when the second transmission ratio is determined as 40% (0.4), the first transmission ratio may be determined as 60% (0.6). According to this, the intensity (size) of the first frequency ultrasonic signal F1 and the intensity (size) of the second frequency ultrasonic signal F2 may be determined. In other words, the transmission ratio determination unit 110 may determine the first transmission ratio and the second transmission ratio so that the sum of the first transmission ratio and the second transmission ratio is 100%.

In addition, according to the above, the transmission ratio may be a ratio of the possible signal intensities (sizes) of the first frequency ultrasonic signal F1 and the second frequency ultrasonic signal F2. However, the present disclosure is not limited thereto, and a description of another embodiment will be described later with reference to FIG. 2.

Figure 2:
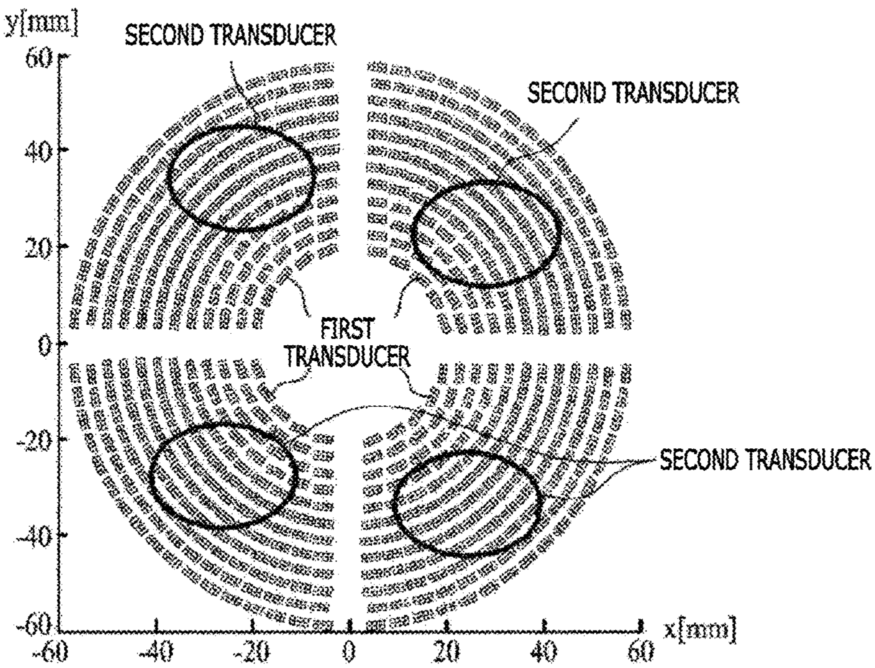
FIG. 2 is a schematic diagram of an ultrasonic transducer of the ultrasonic treatment device that applies the ultrasonic signal generation method for cavitation bubble control according to one embodiment of the present disclosure.
Figure 2:
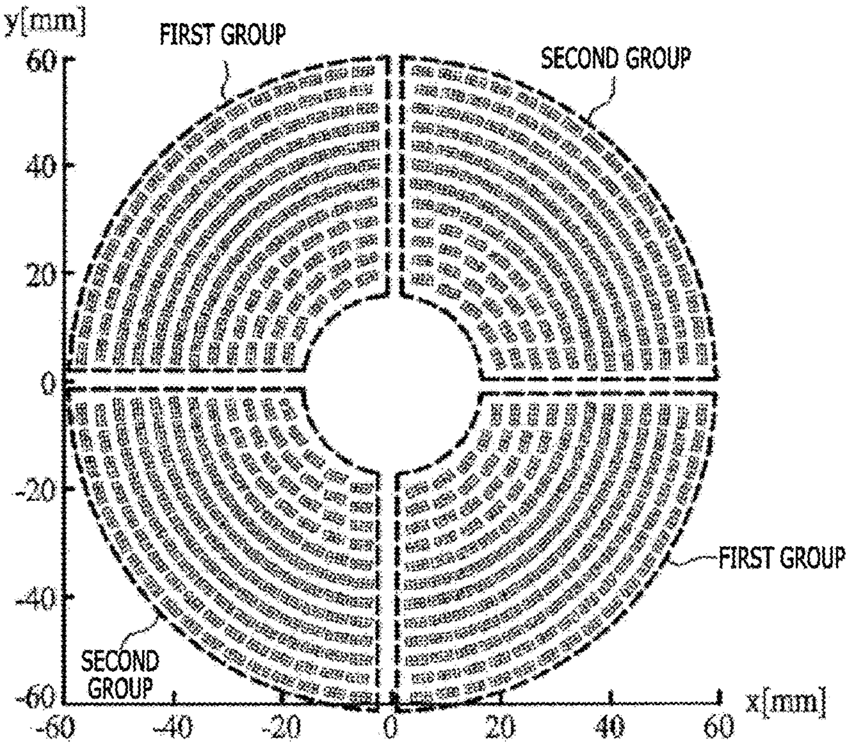

FIG. 2 is a schematic diagram of an ultrasonic transducer of an ultrasonic treatment device that applies an ultrasonic signal generation method for cavitation bubble control according to one embodiment of the present disclosure.

FIG. 2 may be an example of an ultrasonic generator of the ultrasonic probe (not illustrated). The ultrasonic generator illustrated in FIG. 2 may be the first transducer 120 and the second transducer 130. In this case, although the image transducer 140 is not illustrated in FIG. 2, the image transducer 140 may be disposed in the center of a plurality of first transducers 120 and a plurality of second transducers 130 that are actually arranged in a circle. However, the present disclosure is not limited thereto.

In this case, the first transducer 120 may generate the first frequency ultrasonic signal F1 toward the target area so that the cavitation bubble expands in the target area based on the first transmission ratio of the first frequency ultrasonic signal F1 determined by the transmission ratio determination unit 110. In addition, the second transducer 130 may generate the second frequency ultrasonic signal F2 toward the target area so that the expansion of the cavitation bubble in the target area stops, or the cavitation bubble is reduced or eliminated, based on the second transmission ratio of the second frequency ultrasonic signal F2 determined by the transmission ratio determination unit 110.

In other words, the first transducer 120 generates the first frequency ultrasonic signal F1 described above, the second transducer 130 generates the second frequency ultrasonic signal F2 described above, and the transmission ratio determination unit 110 may determine (control) the first transmission ratio, which is the transmission ratio of the first frequency ultrasonic signal F1 generated from the first transducer 120, and determine (control) the second transmission ratio, which is the transmission ratio of the second frequency ultrasonic signal F2 generated from the second transducer 130.

Referring to FIG. 2, the plurality of first transducer 120 and the plurality of second transducer 130 may be formed and arranged randomly within the ultrasonic generator ((a) of FIG. 2), or may be arranged to form a specific group according to at least two or more distinct areas of the ultrasonic generator ((b) of FIG. 2). In this case, the plurality of first transducers 120 and the plurality of second transducers 130 may be formed according to the embodiment, but physically, they mean one identical transducer, but for convenience of explanation, a channel that generates the first frequency ultrasonic signal F1 may be referred to as the first transducer 120, and a channel that generates a second frequency ultrasonic signal F2 may be referred to as the second transducer 130, so that they may be described separately as the first transducer 120 and the second transducer 130.

According to one embodiment of the present disclosure, the transmission ratio determined by the transmission ratio determination unit 110 may be a ratio of the possible signal intensities (sizes) of the first frequency ultrasonic signal F1 and the second frequency ultrasonic signal F2 as described above. However, the present disclosure is not limited thereto, and may be a ratio of the ON/OFF of the plurality of first transducers 120 and the plurality of second transducers 130, or a plurality of channels of the first transducer 120 and a plurality of channels of the second transducer 130.

For example, when the transmission ratio determination unit 110 determines the first transmission ratio as 100% and the second transmission ratio as 20%, the first transducer 120 may turn on all channels, and the second transducer 130 may turn on only 20% of the total channels. In other words, the ratio of channels turned on may be determined according to the transmission ratio determined by the transmission ratio determination unit 110.

According to one embodiment of the present disclosure, the transmission ratio may be determined according to a user input or a treatment control command. For example, when a user inputs the transmission ratio through a control panel or the like included in the device body (not illustrated), the transmission ratio determination unit 110 may determine the transmission ratio based on the input. Alternatively, the transmission ratio determination unit 110 may adjust and determine the transmission ratio for controlling the appropriate cavitation bubble based on the state of the cavitation bubble in the target area monitored by the image transducer 140 described below. In this case, the transmission ratio determination unit 110 may include an artificial intelligence function, and may control the transmission ratio according to the state of the cavitation bubble based on the artificial intelligence function.

According to one embodiment of the present disclosure, the first transducer 120 and the second transducer 130 may simultaneously generate the first frequency ultrasonic signal F1 and the second frequency ultrasonic signal F2 or may alternately generate them. In other words, the first transducer 120 and the second transducer 130 may simultaneously transmit ultrasonic signals at respective frequencies and respective transmission ratios to a target area of the same focus, and may transmit ultrasonic signals by turning on/off some of the plurality of channels according to each transmission ratio at regular time intervals. However, the present disclosure is not limited thereto, and the first transducer 120 and the second transducer 130 may generate ultrasonic signals according to each transmission ratio toward the target area under the condition that the first transducer and second transducer do not affect the ultrasonic signals thereof.

According to one embodiment of the present disclosure, the image transducer 140 may transmit the diagnostic ultrasonic wave to the target area and receive an ultrasound echo signal reflected from the target area to generate an ultrasonic image. Specifically, the image transducer 140 may monitor at least one of the location of the lesion in the target area, whether a cavitation bubble in the target area is eliminated, and whether the lesion is removed.

Specifically, the image transducer 140 may monitor the target area for the lesion of the tissue. The first transducer 120 and the second transducer 130 may focus to emit the ultrasonic signal toward the target area monitored and discovered by the image transducer 140. Next, the first transducer 120 may transmit (apply) the first frequency ultrasonic signal F1 to the target area to generate and expand the cavitation bubble to remove the lesion. In this case, the image transducer 140 monitors whether the lesion in the target area is removed, and the transmission ratio determination unit 110 may control the first transmission ratio and the second transmission ratio according to whether the lesion is removed. When the lesion is not removed, the first transmission ratio may be maintained high, and when the removal is completed, the first transmission ratio may be lowered but the second transmission ratio may be set high so that the cavitation bubble is eliminated. In addition, the image transducer 140 may monitor the state of the cavitation bubble in the target area. When the cavitation bubble that has occurred and expanded in the target area has reached the state that the tissue around the target area is damaged, the transmission ratio determination unit 110 may increase the second transmission ratio to reduce the cavitation bubble even when the lesion is not completely removed.

In addition, the present disclosure is not limited thereto, and the ultrasonic treatment device 100 may simultaneously perform the removal of the lesion through the generation and expansion of the cavitation bubbles and the reduction and elimination of the excessively generated and expanded cavitation bubbles, by simultaneously applying the first frequency ultrasonic signal F1 and the second frequency ultrasonic signal F2 to one target area.

In other words, the ultrasonic treatment device 100 may remove the lesion in the target area by generating the cavitation bubble by applying a first frequency ultrasonic signal F1, and eliminate the cavitation bubble in the target area by applying the second frequency ultrasonic signal F2 at the same time as applying the first frequency ultrasonic signal F1.

Figure 3:
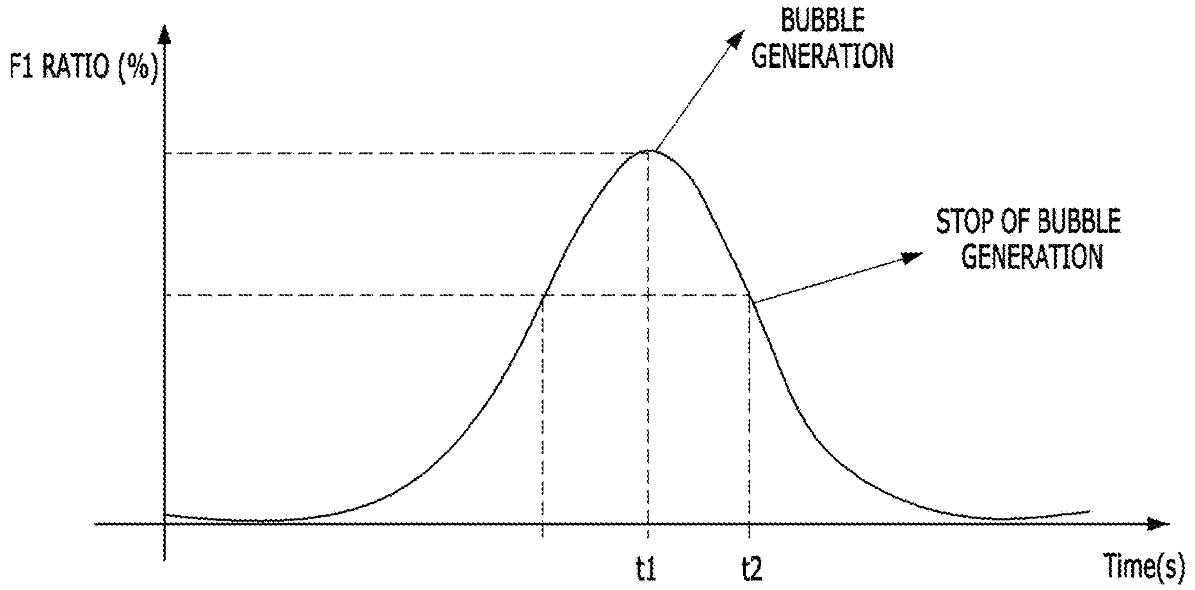
FIG. 3 is an exemplary diagram for explaining cavitation bubble control according to frequency control of the ultrasonic treatment device that applies the ultrasonic signal generation method for cavitation bubble control according to one embodiment of the present disclosure.

FIG. 3 is an exemplary diagram for explaining cavitation bubble control according to frequency control of the ultrasonic treatment device that applies the ultrasonic signal generation method for cavitation bubble control according to one embodiment of the present disclosure.

Referring to FIG. 3, as an example, when the first transducer 120 transmits the first frequency ultrasonic signal F1 according to the first transmission ratio to the target area, and the transmission ratio determination unit 110 gradually increases the first transmission ratio, the cavitation bubbles begin to be generated at a certain time point t1, and the lesion is removed using the cavitation bubbles. Moreover, when it is determined through the monitoring result of the image transducer 140 that cavitation bubbles are excessively generated, the transmission ratio determination unit 110 gradually reduces the first transmission ratio so that the generation of cavitation bubbles may be stopped (t2). In this case, the transmission ratio determination unit 110 may reduce or eliminate the cavitation bubbles by simultaneously reducing the first transmission ratio and increasing the second transmission ratio.

Figure 4:
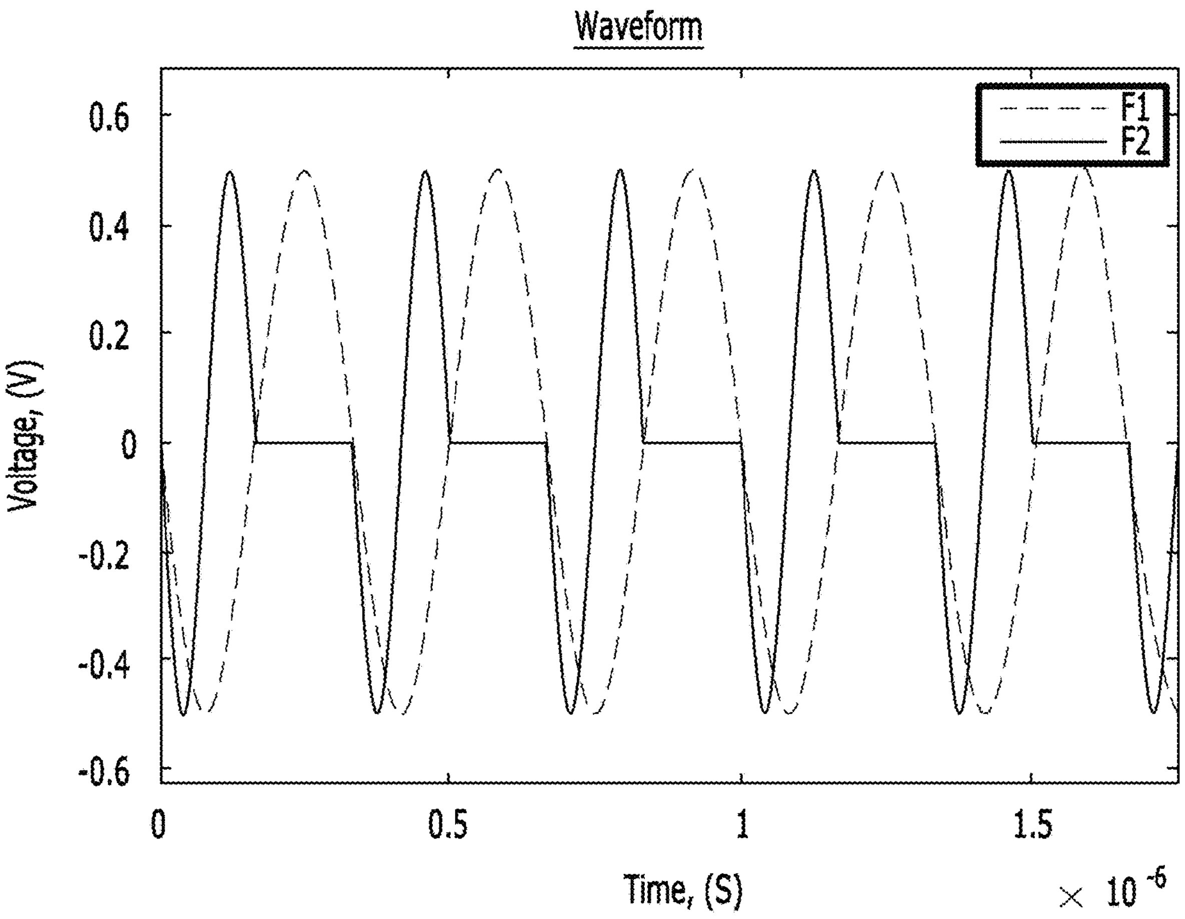
FIG. 4 is an exemplary diagram illustrating waveforms of a plurality of frequencies according to one embodiment of the present disclosure.
Figure 5:
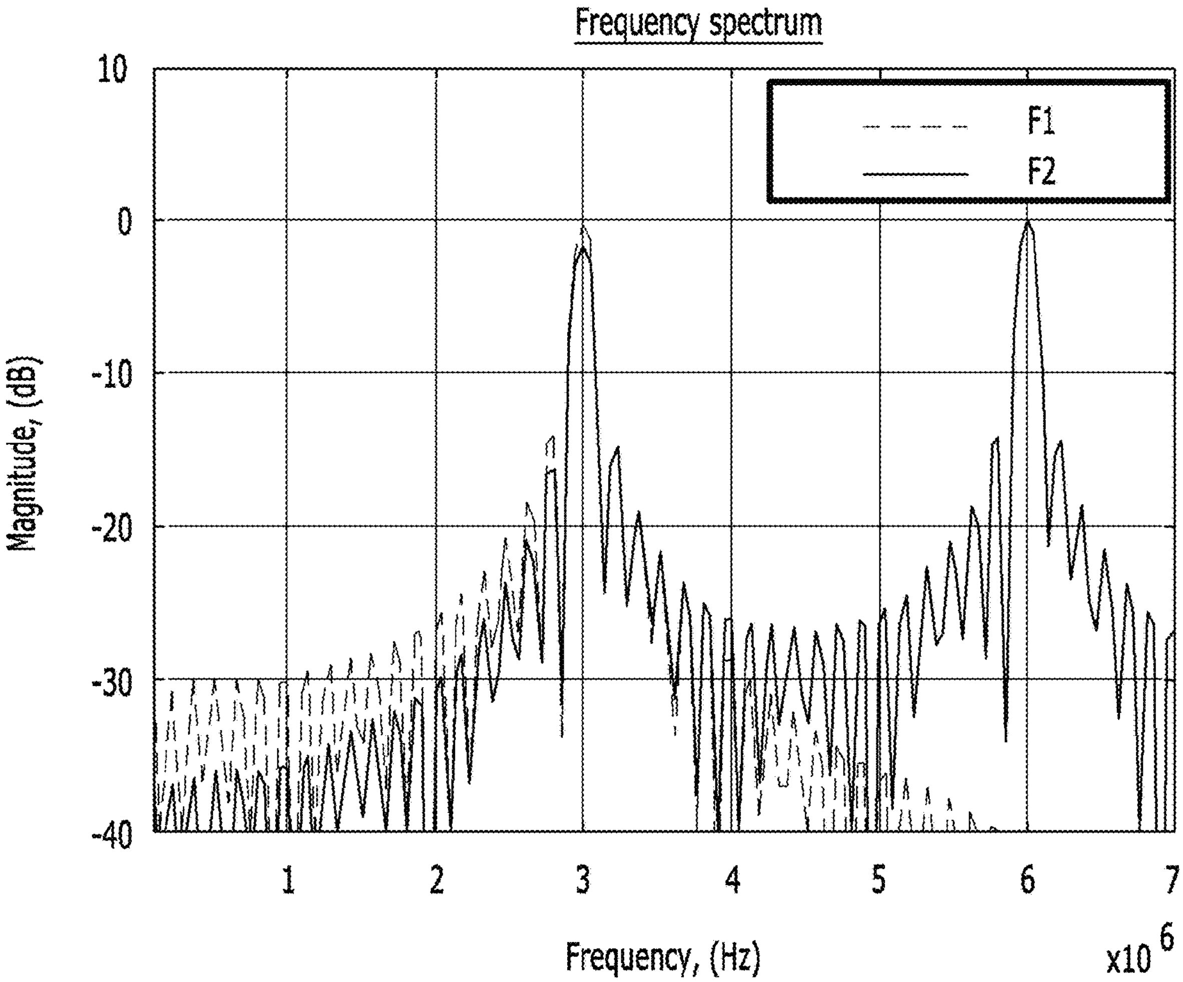
FIG. 5 is an exemplary diagram illustrating frequency spectra of the plurality of frequencies according to one embodiment of the present disclosure.

FIG. 4 is an exemplary diagram illustrating waveforms of a plurality of frequencies according to one embodiment of the present disclosure. In addition, FIG. 5 is an exemplary diagram illustrating frequency spectra of the plurality of frequencies according to one embodiment of the present disclosure.

Referring to FIG. 4, when the first transducer 120 transmits the first frequency ultrasonic signal F1 according to a continuous cycle and the second transducer 130 generates the second frequency ultrasonic signal F2 at the same time as the first frequency ultrasonic signal F1 is generated, a first cycle at which the second frequency ultrasonic signal F2 is transmitted and a second cycle at which the second frequency ultrasonic signal F2 is not transmitted are repeated to generate the second frequency ultrasonic signal F2. In other words, the second transducer 130 may generate the second frequency ultrasonic signal in the form of an interval harmonic.

Figure 6:
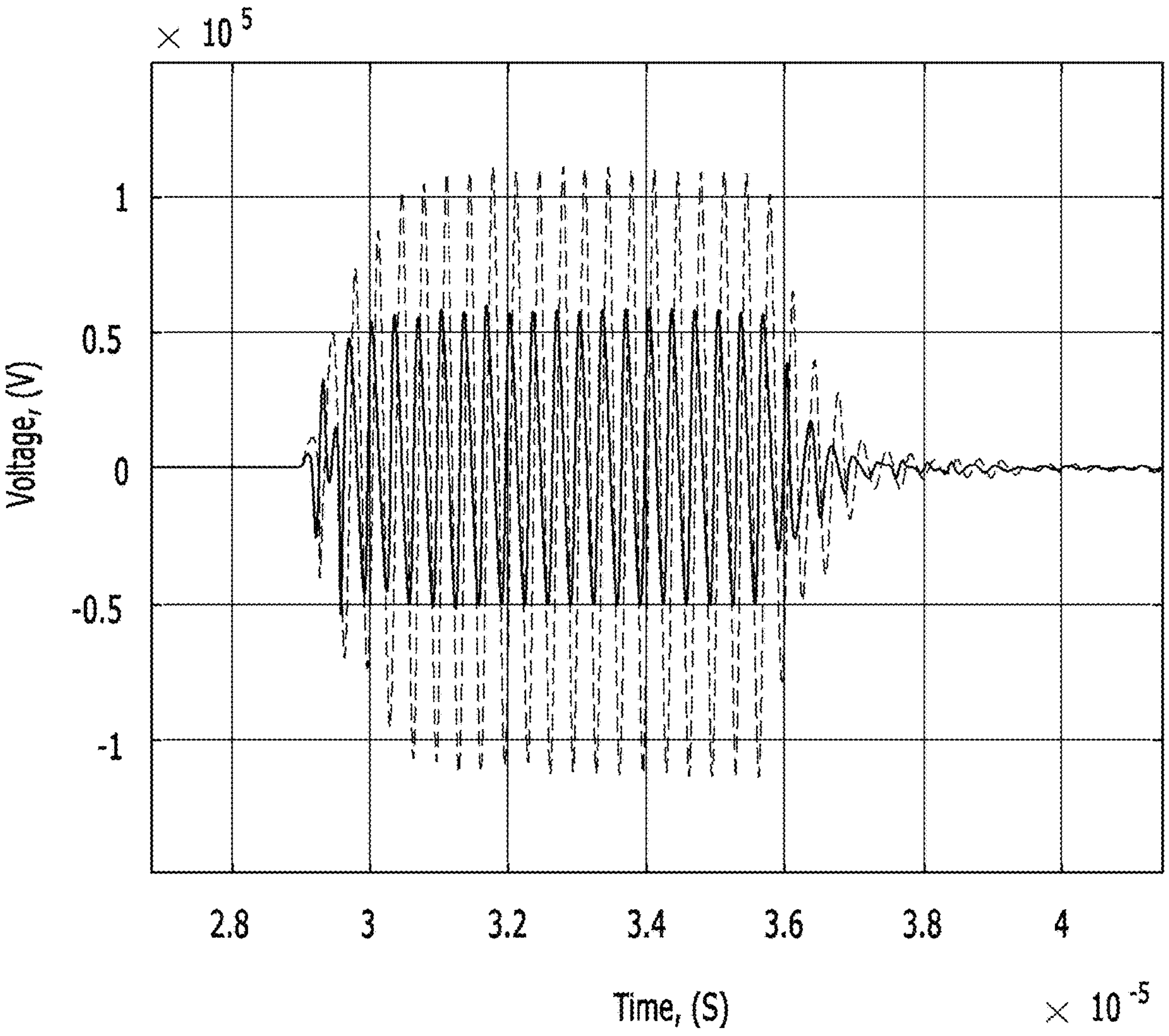
FIG. 6 is an exemplary diagram illustrating radiation waveforms of the plurality of frequencies according to one embodiment of the present disclosure.

FIG. 6 is an exemplary diagram illustrating radiation waveforms of a plurality of frequencies according to one embodiment of the present disclosure. In addition, FIG. 7 is an exemplary diagram illustrating frequency spectra of radiation of a plurality of frequencies according to one embodiment of the present disclosure.

Figure 7:
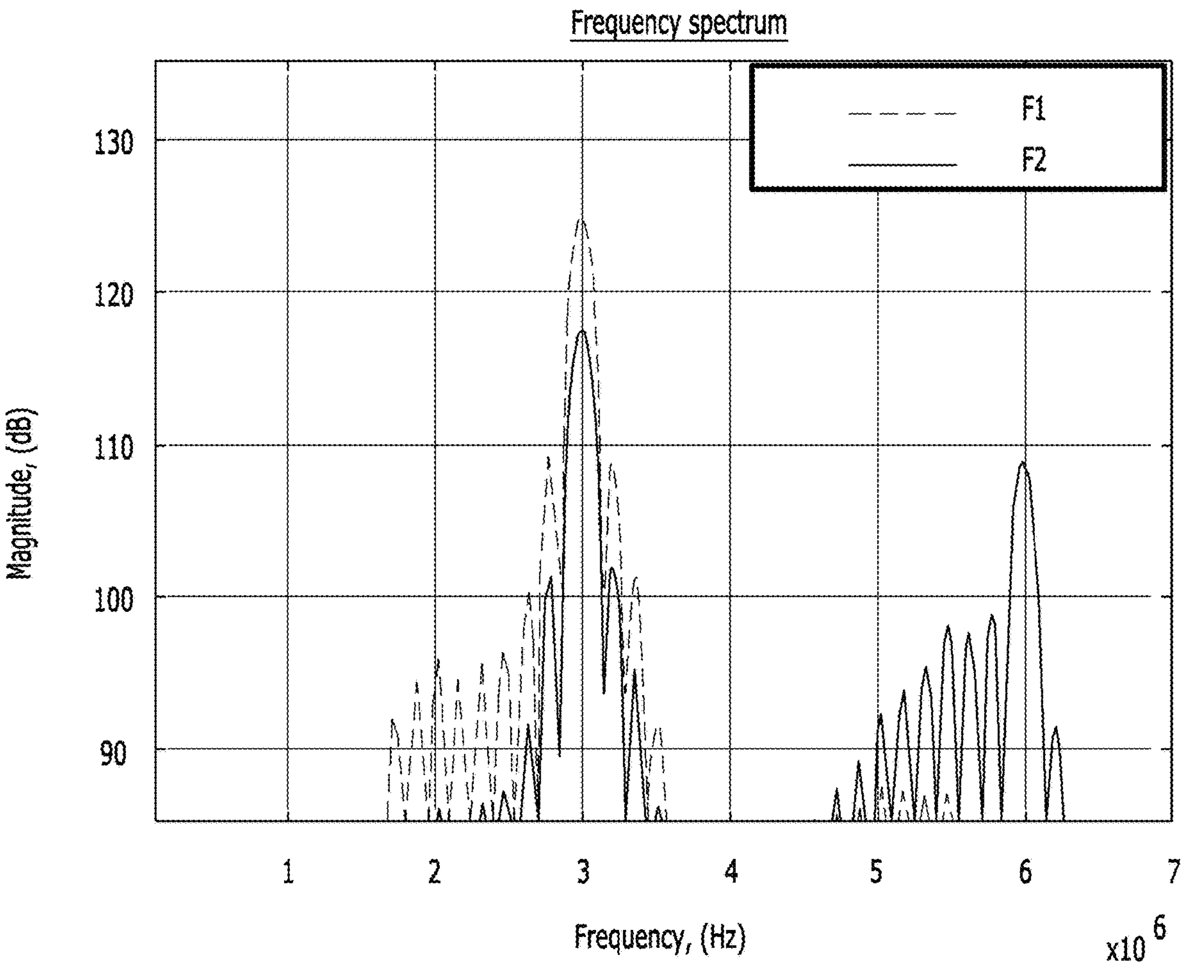
FIG. 7 is an exemplary diagram illustrating frequency spectra of radiation of the plurality of frequencies according to one embodiment of the present disclosure.

Referring to FIGS. 6 and 7, the first frequency ultrasonic signal F1 generated from the ultrasonic treatment device 100 has a uniform frequency characteristic but a reduced radiation pressure, and the second frequency ultrasonic signal F2 may also apply pressure having a uniform frequency characteristic at the same time.

Accordingly, since the frequency characteristics may be stable even when the second frequency ultrasonic signal F2 is applied at the same time as the first frequency ultrasonic signal F1, the lesion may be treated (removed) by applying the first frequency ultrasonic signal F1 to generate or expand the cavitation bubble, and at the same time, the second frequency ultrasonic signal F2 may be applied to reduce or eliminate the cavitation bubble in the area where the treatment has been completed or the excessive cavitation bubble in the same area where the first frequency ultrasonic signal F1 is applied. In other words, the ultrasonic treatment device 100 may simultaneously perform the treatment of the lesion and the control of the cavitation bubble, thereby resolving the problem that the treatment had to be stopped during the frequency modulation time, thereby improving the treatment efficiency.

According to one embodiment of the present disclosure, the first frequency ultrasonic signal F1 may be an ultrasonic signal having a frequency of 3 MHz, and the second frequency ultrasonic signal F2 may be an ultrasonic signal having a frequency of 6 MHz, but is not limited thereto.

As described above, the ultrasonic treatment device 100 according to one embodiment of the present disclosure may simultaneously perform the treatment of the lesion and the control of the cavitation bubble using the plurality of frequencies, thereby solving the problem of decreased treatment efficiency during frequency modulation time, thereby increasing treatment efficiency.

Hereinafter, the operating flow of the present disclosure will be briefly described based on the detailed explanation above.

Figure 8:
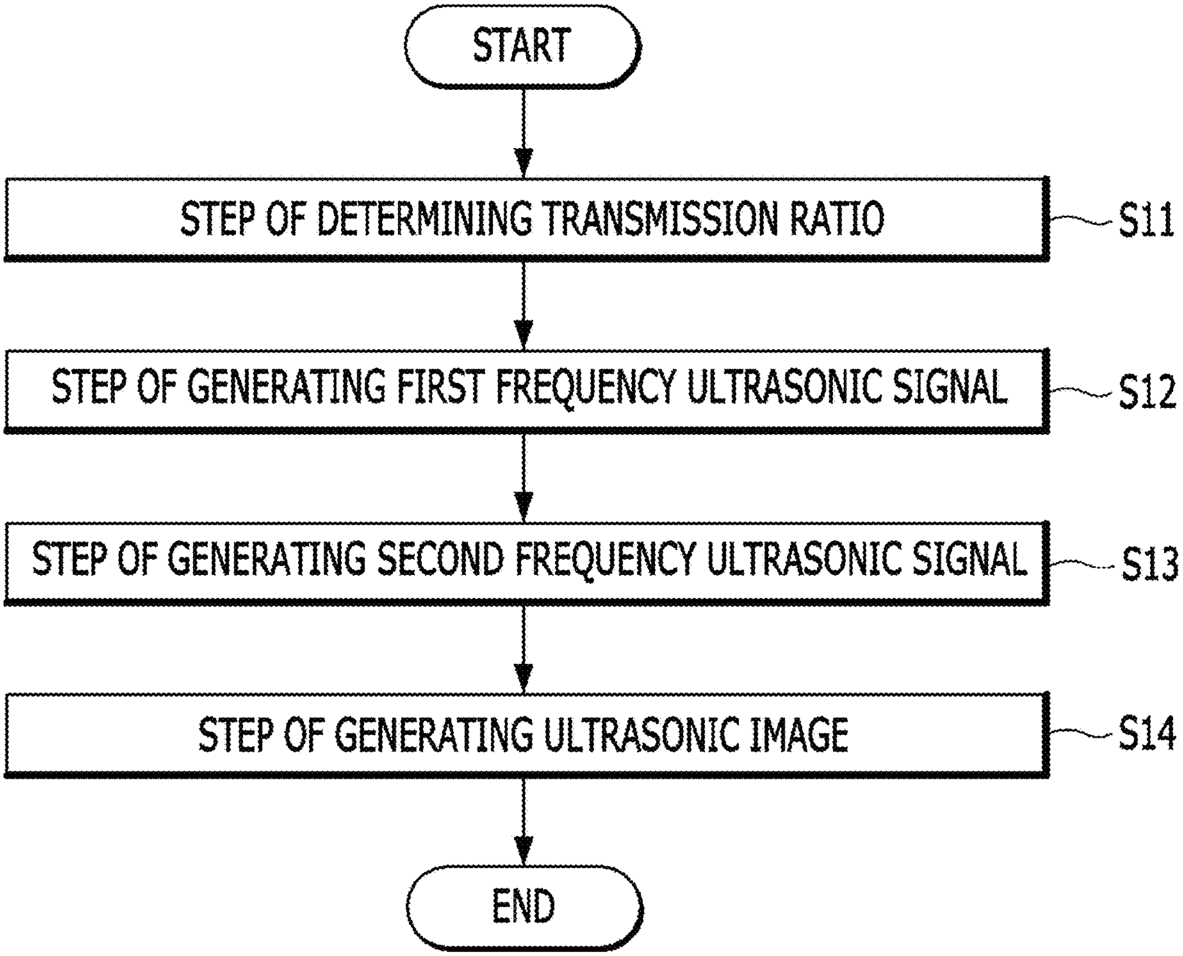
FIG. 8 is an operational flowchart of an ultrasonic signal generation method for cavitation bubble control according to one embodiment of the present disclosure.

FIG. 8 is an operation flow diagram of the ultrasonic signal generation method for cavitation bubble control according to one embodiment of the present disclosure.

The ultrasonic signal generation method for cavitation bubble control illustrated in FIG. 8 may be performed by the ultrasonic treatment device 100 that applies the ultrasonic signal generation method for cavitation bubble control described above. Therefore, even when the content is omitted below, the content described for the ultrasonic treatment device 10 that applies the ultrasonic signal generation method for cavitation bubble control may be equally applied to the description of the ultrasonic signal generation method for cavitation bubble control.

Referring to FIG. 8, in Step S11, the transmission ratio determination unit 110 may determine the transmission ratios of the first frequency ultrasonic signal F1 and the second frequency ultrasonic signal F2. Specifically, in Step S11, the transmission ratio determination unit 110 may determine the first transmission ratio for the first frequency ultrasonic signal F1 and the second transmission ratio for the second frequency ultrasonic signal F2, and may determine the combination ratio of the first frequency ultrasonic signal F1 and the second frequency ultrasonic signal F2 such that the sum of the first transmission ratio for the first frequency ultrasonic signal F1 and the second transmission ratio for the second frequency ultrasonic signal F2 becomes 1 (100%).

Next, in Step S12, the first transducer 120 may generate the first frequency ultrasonic signal F1 toward the target area so that the cavitation bubble expands in the target area based on the transmission ratios. In this case, the first frequency ultrasonic signal F1 may be the signal that generates the cavitation bubble in the target area or expands the cavitation bubble generated in the target area.

Next, in Step S13, the second transducer 130 may generate the second frequency ultrasonic signal F2 toward the target area to stop expansion of the cavitation bubble based on the transmission ratio. In this case, the second frequency ultrasonic signal F2 may be the signal that stops the expansion of the cavitation bubble generated in the target area, or reduces or eliminates the cavitation bubble generated in the target area.

In addition, Steps S12 and S13 may be performed simultaneously or alternately. In other words, the first transducer and the second transducer may generate the first frequency ultrasonic signal F1 and the second frequency ultrasonic signal F2 simultaneously or alternately. In addition, when the first transducer 120 transmits the first frequency ultrasonic signal F1 according to the continuous cycle and the second transducer 130 generates the second frequency ultrasonic signal F2 at the same time as the first frequency ultrasonic signal F1 is generated, the first cycle at which the second frequency ultrasonic signal F2 is transmitted and the second cycle at which the second frequency ultrasonic signal F2 is not transmitted are repeated to generate the second frequency ultrasonic signal F2.

Next, in Step S14, the image transducer 140 may transmit diagnostic ultrasound to the target area and receive the ultrasound echo signal reflected from the target area to generate an ultrasonic image. Specifically, in Step S14, the image transducer 140 may monitor at least one of the location of the lesion in the target area, whether the cavitation bubble in the target area is eliminated, and whether the lesion is removed.

In the above description, Steps S11 to S14 may be further divided into additional steps or combined into fewer steps, depending on the implementation example of the present disclosure. In addition, some steps may be omitted as needed, and the order between the steps may be changed.

The ultrasonic signal generation method for controlling cavitation bubbles according to an embodiment of the present disclosure may be implemented in the form of a program command that may be executed through various computer means and recorded on a computer-readable medium. The computer-readable medium may include program commands, data files, data structures, or the like, alone or in combination. The program commands recorded on the medium may be those specially designed and configured for the present disclosure or may be those known to and usable by those skilled in the art of computer software. Examples of the computer-readable recording medium include magnetic media such as hard disks, floppy disks, and magnetic tapes, optical media such as CD-ROMs and DVDs, magneto-optical media such as floptical disks, and hardware devices specially configured to store and execute program commands such as ROMs, RAMs, and flash memories. Examples of the program commands include not only machine language codes generated by a compiler, but also high-level language codes that may be executed by a computer using an interpreter, or the like. The above hardware devices may be configured to operate as one or more software modules to perform the operations of the present disclosure, and vice versa.

In addition, the ultrasonic signal generation method for controlling cavitation bubbles described above may also be implemented in the form of a computer program or application executed by a computer stored in a recording medium.

The above description of the present disclosure is for illustrative purposes, and those skilled in the art will understand that it may be easily modified into other specific forms without changing the technical idea or essential features of the present disclosure. Therefore, it should be understood that the embodiments described above are exemplary in all respects and not restrictive. For example, each component described as a single component may be implemented in a distributed manner, and likewise, components described as distributed may be implemented in a combined form.

The scope of the present disclosure is indicated by the claims described below rather than the detailed description above, and all changes or modifications derived from the meaning and scope of the claims and their equivalent concepts should be interpreted as being included in the scope of the present disclosure.

The invention claimed is:

1. An ultrasonic signal generation method for cavitation bubble control, the ultrasonic signal generation method comprising:

determining, by a transmission ratio determination unit, transmission ratios of a first frequency ultrasonic signal and a second frequency ultrasonic signal;

generating, by a first transducer, the first frequency ultrasonic signal toward a target area so that a cavitation bubble expands in the target area based on the transmission ratios; and generating, by a second transducer, the second frequency ultrasonic signal toward the target area so that the expansion of the cavitation bubble stops based on the transmission ratios, wherein the determining of the transmission ratios comprises adjusting, by the transmission ratio determination unit, the transmission ratios based on monitoring results obtained from an ultrasonic image of the target area, the monitoring results indicating whether the cavitation bubble in the target area is eliminated and whether a lesion in the target area is removed.

2. The ultrasonic signal generation method of claim 1, wherein the generating of the first frequency ultrasonic signal and the generating of the second frequency ultrasonic signal are performed simultaneously or alternately.

3. The ultrasonic signal generation method of claim 2, wherein in the generating of the first frequency ultrasonic signal, the first frequency ultrasonic signal is transmitted according to a continuous cycle, and wherein in the generating of the second frequency ultrasonic signal, when the second frequency ultrasonic signal is generated simultaneously with the generation of the first frequency ultrasonic signal, a first cycle at which the second frequency ultrasonic signal is transmitted and a second cycle at which the second frequency ultrasonic signal is not transmitted are repeated to generate the second frequency ultrasonic signal.

4. The ultrasonic signal generation method of claim 1, wherein in the determining of the transmission ratios, a first transmission ratio for the first frequency ultrasonic signal and a second transmission ratio for the second frequency ultrasonic signal are determined.

5. The ultrasonic signal generation method of claim 1, wherein in the determining of the transmission ratios, a combination ratio of the first frequency ultrasonic signal and the second frequency ultrasonic signal is determined so that a sum of a first transmission ratio for the first frequency ultrasonic signal and a second transmission ratio for the second frequency ultrasonic signal is 1 (100%).

6. The ultrasonic signal generation method of claim 1, wherein the first frequency ultrasonic signal is a signal that generates the cavitation bubble in the target area or expands the cavitation bubble generated in the target area, and wherein the second frequency ultrasonic signal is a signal that stops the expansion of the cavitation bubble generated in the target area or reduces or eliminates the cavitation bubble generated in the target area.

7. The ultrasonic signal generation method of claim 1, further comprising transmitting a diagnostic ultrasonic wave to the target area and receiving an ultrasonic echo signal reflected from the target area to generate the ultrasonic image.

8. The ultrasonic signal generation method of claim 7, wherein in the generating of the ultrasonic image, at least one of a location of the lesion in the target area, whether the cavitation bubble in the target area is eliminated, and whether the lesion in the target area is removed is monitored.

9. An ultrasonic treatment device for cavitation bubble control, the ultrasonic treatment device comprising:

a transmission ratio determination unit for determining transmission ratios of a first frequency ultrasonic signal and a second frequency ultrasonic signal;

a first transducer for generating the first frequency ultrasonic signal toward a target area so that a cavitation bubble expands in the target area based on the transmission ratios; and a second transducer for generating the second frequency ultrasonic signal toward the target area so that the expansion of the cavitation bubble stops based on the transmission ratios, wherein the transmission determination unit adjusts the transmission ratios based on monitoring results obtained from an ultrasonic image of the target area, the monitoring results indicating whether the cavitation bubble in the target area is eliminated and whether a lesion in the target area is removed.

10. The ultrasonic treatment device of claim 9, wherein the first transducer and the second transducer generate the first frequency ultrasonic signal and the second frequency ultrasonic signal simultaneously or alternately.

11. The ultrasonic treatment device of claim 10, wherein the first transducer transmits the first frequency ultrasonic signal according to a continuous cycle, and wherein when the second frequency ultrasonic signal is generated simultaneously with the generation of the first frequency ultrasonic signal, the second transducer repeats a first cycle at which the second frequency ultrasonic signal is transmitted and a second cycle at which the second frequency ultrasonic signal is not transmitted to generate the second frequency ultrasonic signal.

12. The ultrasonic treatment device of claim 9, wherein the transmission ratios include a first transmission ratio for the first frequency ultrasonic signal and a second transmission ratio for the second frequency ultrasonic signal.

13. The ultrasonic treatment device of claim 9, wherein the transmission ratio determination unit determines a combination ratio of the first frequency ultrasonic signal and the second frequency ultrasonic signal so that a sum of a first transmission ratio for the first frequency ultrasonic signal and a second transmission ratio for the second frequency ultrasonic signal is 1 (100%).

14. The ultrasonic treatment device of claim 9, wherein the first frequency ultrasonic signal is a signal that generates the cavitation bubble in the target area or expands the cavitation bubble generated in the target area, and wherein the second frequency ultrasonic signal is a signal that stops the expansion of the cavitation bubble generated in the target area or reduces or eliminates the cavitation bubble generated in the target area.

15. The ultrasonic treatment device of claim 9, further comprising an image transducer that transmits a diagnostic ultrasonic wave to the target area and receives an ultrasonic echo signal reflected from the target area to generate the ultrasonic image.

16. The ultrasonic treatment device of claim 15, wherein the image transducer monitors at least one of a location of the lesion in the target area, whether the cavitation bubble in the target area is eliminated, and whether the lesion in the target area is removed.

* * * * *